United States Patent [19]
Osborn, III

[11] Patent Number: 5,484,430
[45] Date of Patent: Jan. 16, 1996

[54] SANITARY NAPKIN HAVING TRANSVERSELY SEGMENTED CORE

[75] Inventor: Thomas W. Osborn, III, Cincinnati, Ohio

[73] Assignee: The Procter & Gamble Company, Cincinnati, Ohio

[21] Appl. No.: 129,900

[22] Filed: Sep. 30, 1993

Related U.S. Application Data

[63] Continuation of Ser. No. 827,555, Jan. 28, 1992, abandoned, which is a continuation of Ser. No. 630,451, Dec. 19, 1990, abandoned.

[51] Int. Cl.$^6$ ............................................... A61F 13/15
[52] U.S. Cl. ........................................ 604/385.1; 604/387
[58] Field of Search ........................... 602/40–47, 58, 602/67; 128/849–856; 604/358–402, 304–307

[56] References Cited

U.S. PATENT DOCUMENTS

| | | | |
|---|---|---|---|
| 825,722 | 7/1906 | Greenwald | 604/398 |
| 1,696,205 | 12/1928 | Bombard et al. | 604/375 |
| 2,043,325 | 6/1936 | Jackson, Jr. | 604/378 |
| 2,699,779 | 1/1955 | Lustig | 604/307 |
| 2,747,575 | 5/1956 | Mercer . | |
| 2,771,882 | 11/1956 | Leupold . | |
| 3,071,138 | 1/1963 | Garcia | 604/397 |
| 3,441,023 | 4/1969 | Rijssenbeek | 128/156 |
| 3,653,382 | 4/1972 | Easley et al. . | |
| 3,667,466 | 6/1972 | Ralph | 604/364 |
| 3,848,599 | 11/1974 | Schaar | 604/374 |
| 3,885,568 | 5/1975 | Schaar | 604/385.1 |
| 3,941,132 | 3/1976 | Lenaghan | 604/377 |
| 3,954,107 | 5/1976 | Chesky et al. | 128/290 |
| 3,965,905 | 6/1976 | Schoenholz et al. | 604/377 |
| 4,029,100 | 6/1977 | Karami | 604/374 |
| 4,216,773 | 8/1980 | Ryan . | |
| 4,531,945 | 7/1985 | Allison | 604/378 |
| 4,589,876 | 5/1986 | Van Tilburg | 604/385 R |
| 4,596,570 | 6/1986 | Jackson et al. . | |
| 4,597,759 | 7/1986 | Johnson | 604/385.1 |
| 4,631,062 | 12/1986 | Lassen et al. . | |
| 4,673,403 | 6/1987 | Lassen et al. . | |
| 4,687,478 | 8/1987 | Van Tilburg | 604/387 |
| 4,758,240 | 7/1988 | Glassman | 604/379 |
| 4,773,905 | 9/1988 | Molee et al. | 604/378 |
| 4,795,483 | 1/1989 | Wolfe | 604/385.1 |
| 4,988,344 | 1/1991 | Reising et al. | 604/358 |
| 5,026,363 | 6/1991 | Pratt | 604/377 |
| 5,062,840 | 11/1991 | Holt et al. | 604/385.1 |
| 5,171,302 | 12/1992 | Buell | 604/358 |
| 5,176,672 | 1/1993 | Bruemmer et al. | 604/378 |

FOREIGN PATENT DOCUMENTS

| | | | |
|---|---|---|---|
| 0594443 | 3/1960 | Canada | 604/379 |
| 767336 | 9/1967 | Canada | 604/366 |
| 0076374 | 3/1950 | Norway | 604/386 |
| 20040 | of 1897 | United Kingdom | 604/368 |
| 0472203 | 9/1937 | United Kingdom | 601/374 |
| 9004956 | 5/1990 | WIPO | 604/387 |

*Primary Examiner*—Randall L. Green
*Assistant Examiner*—K. M. Reichle
*Attorney, Agent, or Firm*—Jeffrey V. Bamber; Kevin C. Johnson; Steven W. Miller

[57] ABSTRACT

Disclosed is a sanitary napkin having a transversely segmented absorbent core. The core is divided into a plurality of independent segments, each able to move in the Z-direction without constraints from such movement imposed by adjacent segments. Each segment may be disconnected from the adjacent segment, or connected to the adjacent segment by an isthmic connection registered with the longitudinal centerline of the sanitary napkin or by two isthmic connections, one registered with each longitudinal side edge of the core.

6 Claims, 2 Drawing Sheets

SANITARY NAPKIN HAVING TRANSVERSELY SEGMENTED CORE

This is a continuation of application Ser. No. 07/827,555, filed on Jan. 28, 1992, which was a continuation of application Ser. No. 07/630,451, which was filed on Dec. 19, 1990, now both abandoned.

FIELD OF THE INVENTION

The present invention relates to sanitary napkins and more particularly to sanitary napkins having segmented cores adapted to better conform to the body of the wearer.

BACKGROUND OF THE INVENTION

The present invention relates to sanitary napkins and more particularly to the core of a sanitary napkin which is transversely segmented into a plurality of independently acting segments. Each segment is free from the constraints against movement imposed by other parts of the core, according to sanitary napkins of the prior art. The absence, and even diminution, of constraints allows each core segment to more accurately, authentically, and comfortably conform to the body of the wearer.

Several attempts have been made in the art to provide a sanitary napkin which properly and advantageously conforms to the body of the wearer. For example, U.S. Pat. No. 3,954,107 issued May 4, 1976 to Chesky et al. discloses a longitudinally articulated sanitary napkin. This napkin features a pair of absorbent pads disposed side-by-side. While this arrangement may provide for good conformance of the sanitary napkin to the right-hand and left-hand body halves of the wearer, such a structure does not provide for, nor accommodate, the front-to-back differences in the shape of the body of the wearer.

U.S. Pat. No. 4,589,876 issued May 20, 1986 to Van Tilburg discloses a sanitary napkin having flaps extending from each longitudinal edge of a central absorbent pad. The flaps preferentially bend at a line of juncture between the flap and the longitudinal edge of the central absorbent pad. However, such line of juncture is also principally longitudinally oriented and does not provide a means for adapting the sanitary napkin to the front-to-back differences in the shape of the body of the wearer.

U.S. Pat. No. 4,773,905 issued Sep. 27, 1988 to Molee et al. discloses a winged sanitary napkin having two transverse hinges formed by compressed areas of the core. This arrangement alleges to allow the sanitary napkin to be readily bent about such hinges. However, because the sanitary napkin is connected by the hinges and the hinges bridge the various portions of the core of the sanitary napkin, significant and unobstructed Z-direction discontinuities between various portion of the core are not feasible unless significant stresses are incurred.

Another series of patents teaches raised central sections which are somewhat adapted to conform to the genitalia of the wearer. For example, U.S. Pat. No. 2,747,575 issued May 29, 1956, to Mercer discloses a catamenial bandage having a laterally gathered body which forms a permanently maintained hump. The catamenial bandage is provided with hump retaining means, such as parallel lines of stitches, so that the hump retains it shape and is inherently form fitting to the body and comfortable. U.S. Pat. Nos. 4,631,062 issued Dec. 23, 1986, to Lassen et al. and 4,673,403 issued Jun. 16, 1987, to Lassen et al. disclose convex upwardly shaped sanitary napkin having a raised profile for disposition within the vestibule of a wearer.

U.S. Pat. No. 4,758,240 issued Jul. 19, 1988 to Glassman discloses a sanitary napkin having a plurality of longitudinal channels and a raised central crest coincident with the longitudinal centerline of the sanitary napkin. However, one shortcoming to all such teachings is that either the raised portion of the sanitary napkin extends throughout its entire longitudinal length, without regard to where such raised portion is most beneficial or properly needed and, such a raised portion may be undesirable in the mons region of the wearer's body.

It is an object of this invention to provide a sanitary napkin which accommodates the front-to-back differences in the shape of the body of the wearer and more accurately and comfortably fits to the body of the wearer throughout the entire longitudinal length of the sanitary napkin. It is also an object of this invention to provide a sanitary napkin which provides for Z-direction discontinuities without incurring significant stresses in adjacent portions of the core. It is also an object of this invention to provide a sanitary napkin which provides for a raised central section only in the portion of the sanitary napkin where such a section provides a benefit to the wearer.

BRIEF SUMMARY OF THE INVENTION

The present invention comprises a sanitary napkin having a longitudinal centerline, two longitudinal side margins, and two lateral side margins. The sanitary napkin has a liquid pervious topsheet and a liquid impervious backsheet at least partially peripherally joined to the topsheet. Between the topsheet and the backsheet is a transversely segmented absorbent core divided into a plurality of independent segments. Each segment is bounded by two longitudinal side edges.

The independent segments of the transversely segmented core may be, dependent upon the chosen embodiment, disconnected from the adjacent segments. Alternatively, the sanitary napkin may comprise an isthmic connection joining adjacent independent segments. Dependent upon the chosen embodiment, there may be one isthmic connection substantially registered with the longitudinal centerline of the sanitary napkin or, alternatively, two isthmic connections, each being substantially registered with the longitudinal side edge of the absorbent core.

BRIEF DESCRIPTION OF THE DRAWINGS

While the Specification concludes with claims particularly pointing out and distinctly claiming the present invention, it is believed the same will be better understood from the following description taken in conjunction with the accompanying drawings wherein like parts are given the same reference numeral, analogous parts are designated with a prime symbol, and:

DETAILED DESCRIPTION OF THE INVENTION

Figure 1:
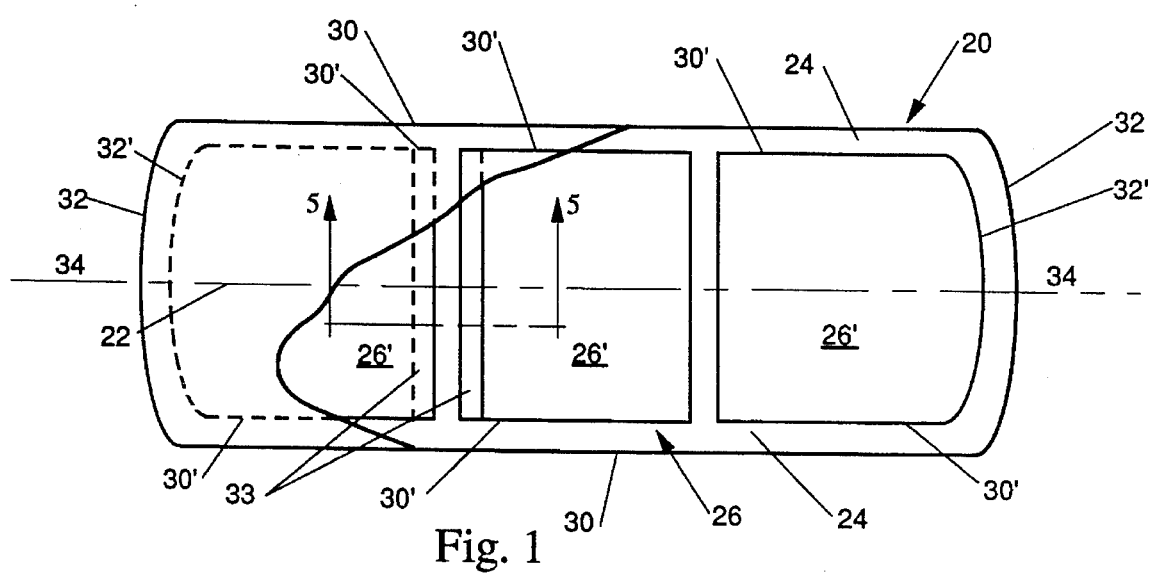
FIG. 1 is a plan view of a sanitary napkin according to the present invention, with the topsheet shown partially in cutaway, and having three independent, disconnected, transversely segmented core segments.

Referring to FIG. 1, in one execution, the invention comprises a sanitary napkin 20. The sanitary napkin 20 is used to collect vaginal discharges, such as menses, and to prevent soiling of the wearer's bedding and clothing by such discharges. The sanitary napkin 20 features a liquid pervious topsheet 22, a liquid impervious backsheet 24, and an absorbent core 26 intermediate the topsheet 22 and the backsheet 24. The perimeter of the sanitary napkin 20 is defined by two longitudinal side margins 30 and two lateral side margins 32.

The sanitary napkin 20 and absorbent core 26 have a longitudinal centerline 34 which conceptually divides the sanitary napkin 20 into two substantially symmetrically opposite halves. As used herein the term "longitudinal" refers to an imaginary line, axis or direction of the sanitary napkin 20 of the absorbent core 26, which line, axis or direction is generally centered between the longitudinal side margins 30 of the absorbent core 26 and is generally aligned with the vertical plane which bisects a standing wearer into left and right body halves. The term "lateral" refers to an imaginary line, axis or direction generally orthogonal the longitudinal direction, within the plane of the sanitary napkin 20 of the absorbent core 26, and is generally sideways aligned relative to the wearer.

Examining the components of the invention in more detail, with continuing reference to FIG. 1, the topsheet 22 is the component of the garment which is oriented towards and contacts the body of the wearer, and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials or perforated polyolefinic films.

The topsheet 22 has a plurality of apertures to permit liquids deposited thereon to pass through to the core 26. An apertured polyolefinic film topsheet 22 having about 5 to about 60 percent open area, typically about 25 percent open area, and a thickness of about 0.01 to about 0.05 millimeters prior to aperturing and about 0.42 to about 0.51 millimeters after aperturing is suitable.

If desired, the topsheet 22 may be sprayed with a surfactant to enhance liquid penetration to the core 26. The surfactant is typically nonionic and should be nonirritating to the skin. A surfactant density of about 0.01 milligrams per square centimeter of topsheet 22 area is suitable. A suitable surfactant is sold by the Glyco Chemical, Inc. of Greenwich, Conn. as Pegosperse 200 ML.

A particularly suitable topsheet 22 may be made in accordance with commonly assigned U.S. Pat. No. 4,342,314 issued Aug. 3, 1982 to Radel et al. and commonly assigned U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Tredegar Corporation of Terre Haute, Ind. has been found to work well.

The backsheet 24 may be any flexible, liquid resistant, preferably liquid impervious material, such as a polyolefinic film. The backsheet 24 prevents discharges collected by and contained in the sanitary napkin 20, and particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.08 millimeters in thickness, preferably about 0.05 millimeters in thickness, has been found to work well. A polyethylene film, such as is sold by the Tredegar Corporation of Terre Haute, Ind., under model X-813 has been found particularly well suited for the backsheet 24.

Alternatively, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and a film such as described in commonly assigned U.S. Pat. No. 4,476,180 issued Oct. 9, 1984 to Wnuk.

In one embodiment, the backsheet 24 is slightly larger than the topsheet 22 and the intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the side margins of the topsheet 22. This geometry provides a marginal area of protection should the core 26 become overloaded or the sanitary napkin 20 otherwise fail. In such an embodiment the backsheet 24 and flaps are preferably unitary and coextensive.

The outwardly oriented face of the backsheet 24 may further comprise a means for attaching the sanitary napkin 20 to the undergarment of the wearer. Pressure sensitive adhesive has been commonly found to work well for this purpose. Preferably a strip of longitudinally oriented adhesive provides good protection against either the front or the back of the sanitary napkin 20 becoming detached from the wearer's undergarment. The adhesive strip may be continuous or intermittent. A particularly preferred arrangement utilizes two longitudinally oriented strips, one on each side of the longitudinal centerline 34.

The topsheet 22 and the backsheet 24 are preferentially peripherally joined using known techniques, either entirely so that the entire perimeter of the sanitary napkin 20 is circumscribed by such joinder or are partially peripherally joined at the perimeter. The term "joined" refers to the condition where a first member or component is affixed to a second member or component either directly; or indirectly, where the first member or component is affixed to an intermediate member or component which in turn is affixed to the second member or component. The joined condition between the first member, or component, and the second member, or component, is intended to remain for the life of the sanitary napkin 20.

The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also helps to provide for a unitary assembly of the sanitary napkin.

Any joined arrangement that provides for capture of the core 26 intermediate the topsheet 22 and the backsheet 24 and a unitary assembly is suitable. Such an assembly has two mutually opposed major faces, one defined by the topsheet 22 and one defined by the backsheet 24.

The absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin.

The core 26 may have a rectangular or hourglass shaped perimeter. The perimeter of the absorbent core 26 is defined by two longitudinal side edges 30' and two lateral side edges 32', which are aligned with the longitudinal and lateral side margins 30 and 32 of the sanitary napkin 20 respectively. The core 26 preferably has two opposed major faces, one oriented towards the backsheet 24 and one oriented towards the topsheet 22 and is generally planar, i.e. does not have significant variations in thickness or isolated macroscopic undulations.

Suitable materials for the core 26 include combinations of airfelt, such as cellulose wadding, and fibrated communition pulp; layers of tissue paper; and absorbent gelling materials. If a tissue paper core 26 is selected, tissue paper made in accordance with commonly assigned U.S. Pat. No. 4,191,609 issued Mar. 4, 1980 to Trokhan and incorporated herein by reference to show a particularly preferred tissue paper core construction for the sanitary napkin 20 described herein. If it is desired to incorporate absorbent gelling materials into the core 26 of the sanitary napkin 20, absorbent gelling materials made in accordance with commonly assigned U.S. Pat. Re. No. 32,649 issued Apr. 19, 1988 to Brandt et al., and incorporated herein by reference for showing particularly preferred absorbent gelling materials, are suitable. A suitable laminate of absorbent gelling materials and tissue may be purchased from the Grain Processing Corporation of Muscatine, Iowa under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

The core 26 should be sized to register with the topsheet 22 and backsheet 24. For ease of manufacturing, the absorbent core 26 should be rectangularly shaped. However, the absorbent core 26 may have arcuate side edges 30' and 32', tapering inwardly as the lateral centerline is approached to provide a generally preferential shaped appearance. The absorbent core 26 may be somewhat hourglass shaped, at the expense of manufacturing difficulties, to provide a generally preferred appearance.

The sanitary napkin 20 according to this invention preferably has a caliper of less than about 4 millimeters and more preferably less than about 6 millimeters (0.24 inches), as measured with a comparator gage having an approximately 80.0 gram test weight, an approximately 10.0 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged liquids from missing the target area.

The core 26 may be joined to the backsheet 24. Joining of the core 26 to the backsheet 24 is preferentially accomplished by adhesively bonding the core 26 to the backsheet 24. Such adhesive (not shown) may be applied in any suitable spray pattern, such as a spiral or longitudinally oriented beads. The adhesive should be surfactant resistant and of low pressure sensitivity, so as not to stick to the skin of the wearer.

The sanitary napkin 20 may also comprise a flap (not shown) extending from a longitudinal side margin 30 of the sanitary napkin 20, and preferably one flap extending from each longitudinal side margin 30 of the sanitary napkin 20. The flaps have a proximal end 36 which is typically coincident with the juncture of attachment of the flap to the longitudinal side margin 30 of the sanitary napkin 20 or, alternatively, the proximal end 36 of the flap may be joined to the sanitary napkin 20 at any other location juxtaposed with the longitudinal side margin 30. The flaps extend laterally outwardly from the sanitary napkin 20 and terminate at a distal end 38 which represents the point of the flap furthest from the longitudinal axis 34 of the sanitary napkin 20.

The flaps may be comprised of an integral and contiguous extension of the topsheet 22, the backsheet 24, or a laminate of both. Alternatively, the flaps may be made of a separate and independent piece of material joined to the longitudinal side margin 30 of the sanitary napkin 20. The flaps are preferably made in accordance with the teachings of commonly assigned U.S. Pat. Nos. 4,589,876 issued May 20, 1986 to Van Tilburg and 4,687,478 issued Aug. 18, 1987 to Van Tilburg.

The core 26 is divided into a plurality of independent segments 26'. Particularly, the segments 26' are transversely independently segmented. As used herein, segments 26' are considered to be "independent" if the segments 26' may have relative movement, in the Z-direction, without being constrained from such movement by an adjacent segment 26'. Cores 26 having fold lines and score lines are not considered to have segments 26' which are "independent" because, constraint from Z-direction movement occurs across the fold line or the score line, even though the fold line or score line may act as a hinge to allow bending of the core 26 at a particular juncture. A core 26 is considered to be transversely segmented when the division between adjacent segments 26' has a vector component within the plane of the core 26 and generally orthogonal the longitudinal axis 34. As used herein, the "Z-direction" refers to the direction generally orthogonal the plane of the core 26 or sanitary napkin 20.

The core 26 may be divided into a plurality of segments 26', preferably three independent segments 26'. A three segment core 26 is desirable because the body of the wearer may be divided into three anatomically distinct shaped regions when the wearer is viewed along the longitudinal axis. From the front of the wearer's body to the back of the wearer's body, the first of the three regions may be thought of as the mons region having a compound curved convex upward shape. The second region is defined by the labia majora and resembles a W-shaped outline. The third region is determined by the gluteal groove and is generally cusp-shaped and defined by two convex upward and outwardly diverging lines. Clearly, a need exists for a sanitary napkin 20 which can adapt to these three very distinct shapes of the wearer's body.

A sanitary napkin 20 according to the present invention may comprise a core 26 having three disconnected segments 26'. Segments 26' of the core 26 are considered to the "disconnected" if the segments 26' are not directly joined to the adjacent segments 26'. However, segments 26' may be considered independent which are indirectly connected, such as through the topsheet 22, backsheet 24, or any tissue wrapping the core 26.

If a sanitary napkin 20 is provided with three segments 26', they need not be of equal length in the longitudinal direction. For example, a sanitary napkin 20 having three segments 26' with the back segment 26' being about 7.0 centimeters (2.75 inches) in longitudinal direction, the center segment 26' being about 7.0 centimeters (2.75 inches), and the front segment 26' being about 6.4 centimeters (2.5 inches) in longitudinal dimension has been found to work well.

The differences in longitudinal dimension between the segments 26' may be accounted for because the central segment 26' which fits the labia majora region of the wearer's body is the most critical to obtain good fit. The second most critical area to obtain good fit occurs in the back portion of the sanitary napkin 20 so that the gluteal groove is accommodated, while the fit of the front of the sanitary napkin 20 to the mons region of the wearer's body is least critical.

Figure 2:
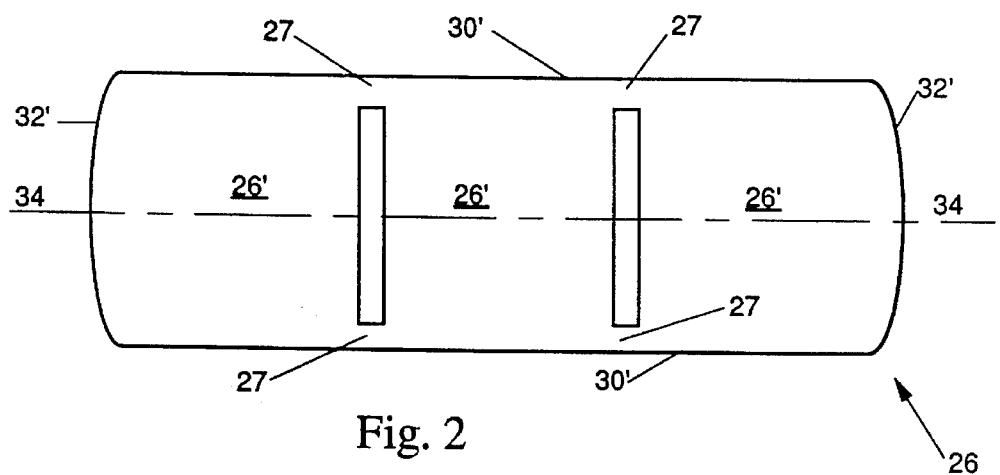
FIG. 2 is a plan view of a sanitary napkin core according to the present invention having three independent segments, each joined to the adjacent segment by two isthmic connections, each isthmic connection substantially registered with a longitudinal side edge of the absorbent core.

Referring to FIG. 2, the core 26 of a sanitary napkin 20 according to the present invention may have independent but connected segments 26'. Segments 26' may be connected through an isthmic connection 27. The isthmic connection 27 preferably comprises not more than about twenty percent, and preferably not more than about ten percent of the width of the core 26 of the sanitary napkin 20. As illustrated in FIG. 2, the isthmic connection 27 may be disposed along the longitudinal edges 30' of the core 26 of the sanitary napkin 20. Such an arrangement provides for maximum relative Z-direction displacement between adjacent segments 26' of the core 26 of the sanitary napkin 20 to occur generally coincident the longitudinal centerline 34 of the sanitary napkin 20. This arrangement is, therefore, particularly desirable for obtaining good conformance of the core 26 of the sanitary napkin 20 to the vaginal opening of the wearer.

Figure 3:
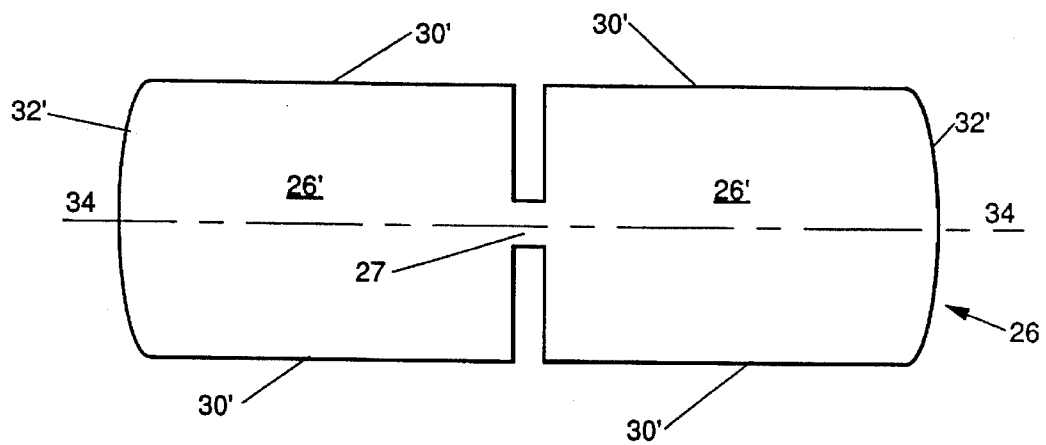
FIG. 3 is a plan view of a sanitary napkin core according to the present invention having two independent segments joined by an isthmic connection registered with the longitudinal centerline of the sanitary napkin.

Referring to FIG. 3, if desired, the core 26 of a sanitary napkin 20 according to the present invention may comprise a plurality of two independent segments 26'. If such an arrangement is selected, the division between these segments 26' should be allocated so that the back segment 26' of the core 26 of the sanitary napkin 20 comprises about twenty percent to about sixty percent of the total longitudinal dimension of the core 26 of the sanitary napkin 20. The front segment 26' of the core 26 may be longer than the rear segment 26', to accommodate the convex upward configurations of both the front and the center regions of the wearer's body, as described above.

Also, as illustrated by FIG. 3, the isthmic connection 27 may be substantially registered with the longitudinal centerline 34 of the sanitary napkin 20. This arrangement provides the advantages that the longitudinal edges 30' of the core 26 of the sanitary napkin 20 are free and maximum Z-direction relative displacement between adjacent segments 26' of the core 26 of the sanitary napkin 20 can occur at such longitudinal edges 30'. However, while this arrangement may provide a more comfortable fit to the wearer, with less chafing against the inner thighs, maximum fit with the vaginal opening may not be obtained.

Figure 4:
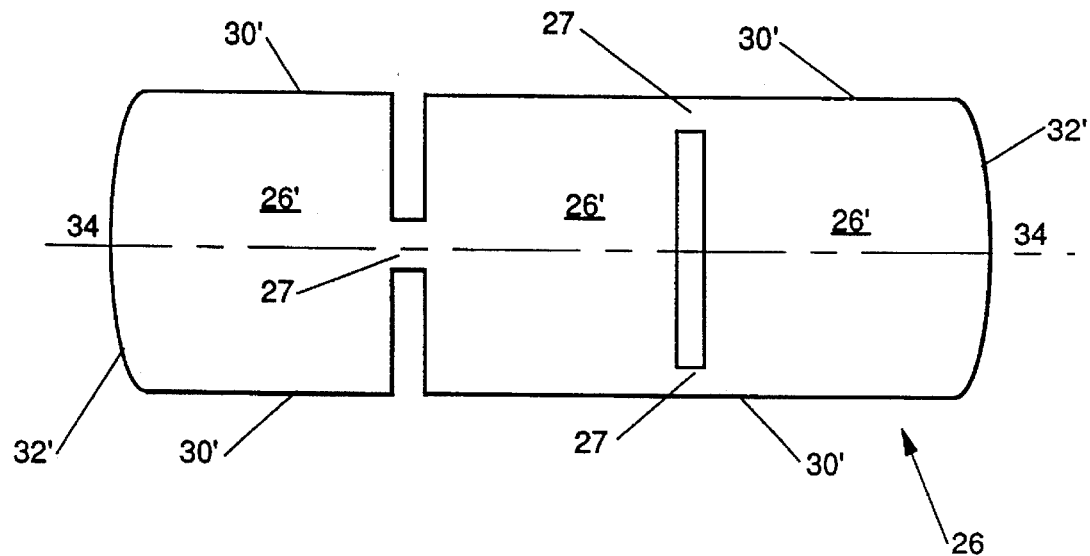
FIG. 4 is a plan view of a hybrid sanitary napkin core according to the present invention having three independent segments, two joined by isthmic connections registered with the longitudinal edges of the core and two joined by an isthmic connection registered with the longitudinal centerline of the sanitary napkin.

Referring to FIG. 4, a hybrid sanitary napkin 20 may be made incorporating the isthmic connections 27 of both FIGS. 2 and 3. Such a sanitary napkin 20 has an isthmic connection 27, registered with the longitudinal centerline 34 and joining the front and center segments 26' of the core 26 of the sanitary napkin 20. This isthmic connection 27 allows the segment 26' of the core 26 registered with the more gradual convex upwardly curved shape of the mons region to have a greater radius of curvature than the segment 26' of the core 26 registered with the sharper, more concave shape of the labia majora region of the wearer's body having a lesser radius of curvature. It will be apparent to one skilled in the art that as the radius of curvature of a particular segment 26' increases, the span between the longitudinal side edges 30' of that segment 26' and between the longitudinal side edges 30' of the sanitary napkin 20 increases.

However, the isthmic connections 27 joining the rear and center segments 26' of the sanitary napkin 20 may be substantially registered with the longitudinal edges of the core 26 of the sanitary napkin 20. This arrangement allows maximum Z-direction displacement of the rear section to occur at the longitudinal centerline 34 of the sanitary napkin 20, so that the rear segment 26' may accurately and comfortably fit into the gluteal groove of the wearer.

If desired, the rear segment 26' of the core 26 may be provided with a longitudinally oriented slit (not shown) to further enhance the fit of the rear segment 26' to the wearer. However, if a slit is provided in the rear segment 26' of the core 26 of the sanitary napkin 20, the slit should not penetrate the backsheet, otherwise leakage onto the clothing and bedding of the wearer may occur.

It is not necessary that the slit in the rear segment 26' of the core 26 of the sanitary napkin 20 be parallel to the longitudinal axis. Instead, the slit may be oriented within about ±45 degrees of the longitudinal axis or resemble a V-shape having its vertex registered with the border between the rear segment 26' and the adjacent segment 26' of the core 26 of the sanitary napkin 20.

Figure 5:
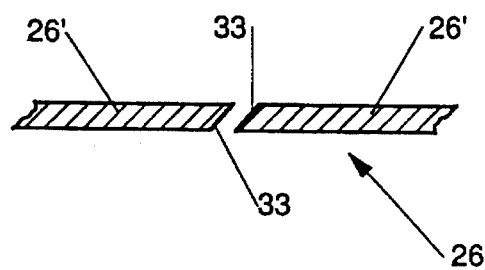
FIG. 5 is an enlarged, fragmentary vertical sectional view taken along line 5—5 of FIG. 1 showing the mutually opposed co-bevelled transverse edges of the core of the sanitary napkin of FIG. 1.

Referring to FIG. 5, if desired, the sanitary napkin 20 may be provided with a means to promote longitudinal movement between adjacent segments 26' of the core 26 of the sanitary napkin 20. Typically, longitudinal movement between the rear and center segments 26' occurs due to forces imparted to the sanitary napkin 20, and its core 26, by body movements of the wearer, such as sitting or lying down.

One means to promote longitudinal movement between adjacent segments 26' of the core is to provide the segments 26' with mutually co-bevelled edges 33. The transverse edges of the segments 26' should be mutually co-bevelled particularly if the core 26 is relatively thick. Most particularly, longitudinal movement may be more readily promoted by providing mutually co-bevelled edges 33 between the rear segment 26' and the adjacent segment 26', so that the rear segment 26' may overlap the adjacent segment 26'. When the rear segment 26' overlaps and is on top of the adjacent segment, the rear segment 26' is interposed between the adjacent segment 26' and the topsheet 22. Edges of the segments 26' of the core 26 are considered to be "mutually co-bevelled" if each edge has a diagonal plane, relative to the Z-direction, which is approximately mutually parallel to the diagonally opposed plane of the edge of the segment 26' of the core 26 which it faces.

It is particularly desirable that if mutually co-bevelled edges 33 are provided, the segments 26' are disconnected so that longitudinal movement is not hindered by the isthmic connections 27 which otherwise allow Z-directional movement.

It will be apparent to one skilled in the art that various other combinations and mutations of the foregoing embodiments may be applied by one skilled in the art, all of which are within in the spirit and scope of the appended claims.

For example, the borders between adjacent segments 26' need not be straight, as shown. Instead, the borders between adjacent segments 26' may be arcuate or comprise a plurality of rectilinear line segments 26' which are diagonal relative to the longitudinal axis 34 of the sanitary napkin 20.

What is claimed is:

1. A sanitary napkin having a longitudinal centerline, two longitudinal side margins, and two lateral side margins, said sanitary napkin comprising:

a liquid pervious topsheet;

a liquid impervious backsheet at least partially peripherally joined to said topsheet;

a transversely segmented absorbent core positioned between said topsheet and said backsheet, said transversely segmented absorbent core being divided into a plurality of independent segments having transverse edges; and a means to promote relative longitudinal movement between adjacent segments of said core which comprises said transverse edges of said independent core segments being mutually co-bevelled.

2. A sanitary napkin according to claim 1 wherein said core has two independent segments.

3. A sanitary napkin according to claim 1 wherein said core has three independent segments.

4. A sanitary napkin according to claim 1 wherein one said segment of said core is a rear segment, said rear segment being adapted to longitudinally move on to the top of said adjacent segment, so that said rear segment is interposed between said adjacent segment and said topsheet.

5. A sanitary napkin according to claim 1 wherein two of said adjacent segments of said segmented core have substantially zero Z-direction relative displacement at the longitudinal centerline and maximum Z-direction relative displacement at the longitudinal side margins of said sanitary napkin.

6. A sanitary napkin according to claim 1 wherein two said adjacent segments of said segmented core have substantially zero Z-direction relative displacement at said longitudinal side margins and maximum Z-direction relative displacement at the longitudinal centerline of said sanitary napkin.

* * * * *